United States Patent [19]

Itatani et al.

[11] Patent Number: 4,567,280

[45] Date of Patent: Jan. 28, 1986

[54] PROCESS FOR PRODUCING IODO-AROMATIC COMPOUNDS

[75] Inventors: Hiroshi Itatani; Mikito Kashima, both of Chiba; Yasutaka Tasaki, Narashino, all of Japan

[73] Assignee: UBE Industries, Ltd., Yamaguchi, Japan

[21] Appl. No.: 646,749

[22] Filed: Sep. 4, 1984

[30] Foreign Application Priority Data

Sep. 6, 1983 [JP] Japan ................................. 58-162637

[51] Int. Cl.$^4$ ............................................. C07C 17/12
[52] U.S. Cl. ..................................... 549/43; 549/434; 549/460; 568/656; 564/412; 564/192; 570/182; 570/183; 570/253

[58] Field of Search ....................... 570/182, 183, 253; 549/460, 43, 434; 568/656; 564/412, 192

Primary Examiner—Paul R. Michl
Assistant Examiner—Alex H. Walker
Attorney, Agent, or Firm—Sherman & Shalloway

[57] ABSTRACT

In a process for producing an iodo-aromatic compound which comprises iodinating an aromatic compound having an electron-donating substituent bonded to the benzene ring with iodine in the presence of a solvent, the improvement wherein about ½ to about 10 moles, per mole of iodine added to the reaction system, of nitrogen dioxide ($NO_2$) is added in the form of $NO_2$ to the reaction system, and the reaction is carried out in the presence of nitrogen dioxide.

10 Claims, No Drawings

PROCESS FOR PRODUCING IODO-AROMATIC COMPOUNDS

This invention relates to an improved process for producing an iodo-aromatic compound by iodinating an aromatic compound having an electron-donating substituent bonded to the benzene ring, such as xylene or diphenyl ether, with iodine in the presence of a solvent. The process can obviate the use of an oxidizing agent which is expensive and/or is difficult to regenerate or cannot be regenerated, and the treatment of the waste water derived from the spent mineral acid can be avoided. In addition, the yield of the iodo-aromatic compound (compound in which the aromatic ring is iodinated) based on the used iodine is high, and the process can advantageously circumvent the undesirable formation of nitration by-products and can give the iodo-aromatic compound in good selectivity.

More specifically, this invention relates, in a process for producing an iodo-aromatic compound which comprises iodinating an aromatic compound having an electron-donating substituent bonded to the benzene ring with iodine in the presence of a solvent, to the improvement wherein at least about $\frac{1}{2}$ mole, preferably about $\frac{1}{2}$ to about 10 moles, per mole of iodine added to the reaction system, of nitrogen dioxide ($NO_2$) is added in the form of $NO_2$ to the reaction system, and the reaction is carried out in the presence of nitrogen dioxide.

Since iodo-aromatic compounds easily undergo ammonolysis and carboxylation under relatively mild reaction conditions, they are useful as materials or intermediates for the productions of specialty chemicals, for example medical drugs, agricultural chemicals, dyestuffs, photosensitive materials, etc.

Various methods have previously been proposed for the production of iodo-aromatic compounds by the iodination of aromatic compounds.

For example, Japanese Laid-Open Patent Publication No. 14527/1974 (laid open on Feb. 5, 1974) describes the production of a styryl compound. It describes an example of producing a starting material used in the production, in which potassium persulfate, concentrated sulfuric acid, biphenyl and iodine are fed into a mixture of glacial acetic acid, water and carbon tetrachloride, they are reacted under refluxing conditions, and an additional amount of potassium persulfate is added and reacted to produce 4,4'-diiodobiphenyl. U.S. Pat. No. 4,240,987 (issued Dec. 23, 1980) describes a process for the direct iodination of polyacrylidene compounds. The U.S. Patent discloses an embodiment in which a polyarylidene compound is iodinated with iodine by using ammonium persulfate/concentrated sulfuric acid in a reaction medium containing a solvent for the polyarylidene compound, a catalyst and water.

These prior methods are industrially unsatisfactory because potassium persulfate and ammonium persulfate used as the oxidizing agent are relatively expensive and cannot be regenerated for further use. They are also industrially disadvantageous because the waste water derived from the spent mineral acid should be treated. In addition, the yields of the iodo-aromatic compounds based on the iodine used are about 90% at the highest. Accordingly, these methods are still desired to be improved.

Other known prior methods include the iodination of toluene with iodine using silver trifluoroacetate as an oxidizing agent [J. Amer. Chem. Soc., vol. 73, 1362 (1951)] and the iodination of p-xylene with iodine using an acetic acid solution of peracetic acid as an oxidizing agent [J. Amer. Chem. Soc., vol. 90, 6187 (1968)].

These methods have the disadvantage that silver trifluoroacetate and peracetic acid used as the oxidizing agent are relatively expensive, and the operations involve a danger. They are also industrially unsuitable because these catalysts are difficult to regenerate. The yields of the iodo-aromatic compounds based on the iodine used are about 85% at the highest.

It is also known to iodinate o-xylene or 4-iodo-o-xylene with iodine using 70% nitric acid in an acetic acid/concentrated sulfuric acid system [J. Org. Chem., vol. 42, No. 25, 4049 (1997)]. This prior art relates to the nitration of 4-iodo-o-xylene, and shows an example in which o-xylene and finely divided iodine are added to a mixture composed of 500 ml of acetic acid and 140 ml of concentrated sulfuric acid, and the iodination is carried out while adding 70% nitric acid dropwise. In regard to the iodination of aromatic compounds with iodine using nitric acid, there are also known the method involving the use of nitric acid having a specific gravity of 1.50 described in Organic Syntheses, coll. vol. 1, 323 (1941), and the method involving the use of nitric acid having a concentration of 50 to 70% by weight described in Japanese Laid-Open Patent Publication No. 77830/1983 (laid open on May 11, 1983).

These methods of iodinating aromatic compounds with iodine using nitric acid cannot avoid the treatment of the waste water derived from the spent mineral acid, and give rise to a new technical problem in that the formation of undesired nitration by-products is difficult to circumvent.

For example, Japanese Laid-open Patent Publication No. 77830/1983 discusses the above-cited method of Organic Syntheses, coll. vol. 1, 323 (1941) as prior art. The above Japanese patent document states that according to the method of Organic Syntheses using fuming nitric acid, nitration of benzene proceeds to give a large amount of by-product nitrobenzene, and that this is operationally dangerous and the removal of this by-product requires complex operations such as the reduction of the nitro group and steam distillation under acidic conditions.

Furthermore, Japanese Laid-Open Patent Publication No. 77830/1983 gives a comparative experiment in which 85% by weight nitric acid was used, and indicates that in this comparative experiment, the nitration by-product was formed in an amount of 28% and the yield of iodobenzene based on the iodine used was as low as 70%. The Japanese patent document states that by using nitric acid having a concentration of 30 to 70% by weight, the amount of the nitration by-product can be reduced, and the yield of iodobenzene based on iodine can be increased. But the highest yield shown in this patent document is 91% and the formation of 0.7% of the nitration by-product cannot be avoided. The prior techniques involving the use of nitric acid including the method shown in this Japanese patent document cannot obviate the treatment of the industrial waste water derived from the spent mineral acid.

It is well known that an aromatic compound having an electron-donating substituent bonded to the benzene ring, such as anisole, more readily undergoes nitration with nitric acid than an aromatic compound having no electron-donating substituent bonded to the benzene ring, such as benzene. In view of this fact, the use of nitric acid for iodination of aromatic compounds having an electron-donating substituent bonded to the benzene ring with iodine only suggests disadvantage.

We have worked extensively in order to develop an improved process which can overcome the technical disadvantages of the aforesaid prior methods, and consequently found that these disadvantages can be overcome if in the production of an iodo-aromatic compound by iodination of an aromatic compound having an electron-donating substituent bonded to the benzene ring with iodine in the presence of a solvent, nitrogen dioxide ($NO_2$) not proposed heretofore is added in the form of $NO_2$ to the reaction system, particularly in an amount of at least about $\frac{1}{8}$ mole, preferably about $\frac{1}{4}$ mole to about 10 moles, per mole of iodine added to the reaction system, and the reaction is carried out in the presence of nitrogen dioxide.

We have found that by carrying out the iodination reaction using $NO_2$ which is inexpensive and easily available, it is possible to obviate the use of an oxidizing agent which is expensive and/or is difficult to regenerate or cannot be regenerated, and the treatment of the waste water derived from the spent mineral acid can be avoided. We have further found that the process of the invention gives the iodo-aromatic compound in a high yield based on the iodine used is advantageously free from the formation of the undesired nitration by-product, and can give the iodo-aromatic compound in good selectivity.

It has also been found that the process of this invention can achieve various advantages suitable for industrial practice. For example, nitrogen monoxide (NO) formed by the reaction can be easily converted to $NO_2$ by oxidation with air, for example, and can be recycled to the reaction system. This is advantageous to the curtailment of the cost of production in industrial practice. Since the selectivity for the formation of the iodo-aromatic compound is high, the iodo-aromatic compound is easy to separate and purify. By properly selecting the solvent used in the reaction, the resulting iodo-aromatic compound can be easily separated by filtration and/or solvent extraction. At this time, the filtrate (mother liquor) and/or the solvent extraction residue can be directly recycled to the reaction system. Furthermore, since the reaction conditions can be mild, troubles associated with the apparatus and corrosion can be avoided.

It is an object of this invention therefore to provide an improved process for producing iodo-aromatic compound which comprises iodinating an aromatic compound having an electron-donating substituent bonded to the benzene ring with iodine in the presence of a solvent.

The above and other objects and advantages of this invention will become more apparent from the following description.

According to the process of this invention, in the production of an iodo-aromatic compound by iodinating an aromatic compound having an electron-donating substituent bonded to the benzene ring with iodine in the presence of a solvent, at least about $\frac{1}{8}$ mole, preferably about $\frac{1}{4}$ mole to about 10 moles, per mole of iodine added to the reaction system, of nitrogen dioxide ($NO_2$) is added in the form of $NO_2$ to the reaction system and the iodination is carried out. Nitrogen monoxide (NO) formed as a result of the reaction can be easily converted to $NO_2$ by oxidizing it with molecular oxygen or a gas containing molecular oxygen such as air, and can be recycled to the reaction system.

One embodiment of the process of this invention is schematically shown below by taking up toluene as an example of the aromatic compound having an electron-donating substituent on the benzene ring.

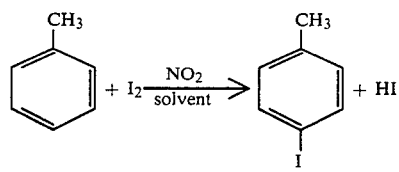

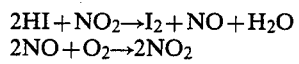

$2HI + NO_2 \rightarrow I_2 + NO + H_2O$ $2NO + O_2 \rightarrow 2NO_2$

Compounds having an aromatic ring and at least one electron-donating substituent bonded to the benzene ring can be widely used as the aromatic compound having an electron-donating substituent bonded to the benzene ring in the process of this invention. These compounds may have a hetero atom-containing ring fused to the aromatic ring.

Examples of the electron-donating substituent include alkyl groups such as those having 1 to 4 carbon atoms, alkoxy groups such as those having 1 to 4 carbon atoms, an amino group, acylamino groups such as $C_2$–$C_5$ acylamino groups, a phenyl group which may be substituted by halogen, a phenoxy group which may be substituted by halogen, a phenylthio group which may be substituted by halogen, a phenylamino group, a phenylazo group, halogen atoms, and groups bonded to the two adjacent carbon atoms of the benzene ring, such as

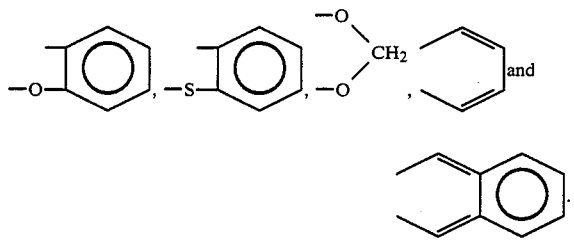

Examples of the aromatic compound having the electron-donating substituent exemplified on the benzene ring are those of the following formula

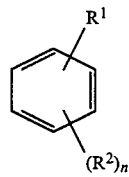

wherein n represents 0, 1 or 2, $R^1$ represents a group selected from the class consisting of lower alkyl groups, lower alkoxy groups, an amino group, lower acylamino groups, a phenyl group which may be substituted by a halogen such as I or Cl, a phenoxy group which may be substituted by a halogen such as I or Cl, a phenylthio group which may be substituted by a halogen atom such as I or Cl, a phenylamino group and a phenylazo group, $R^2$ represents a group selected from the class consisting of lower alkyl groups, lower alkoxy groups, Cl and I, and when n is 1, $R^1$ and $R^2$ together may form a group bonded to the adjacent carbon atoms of the benzene ring, i.e.

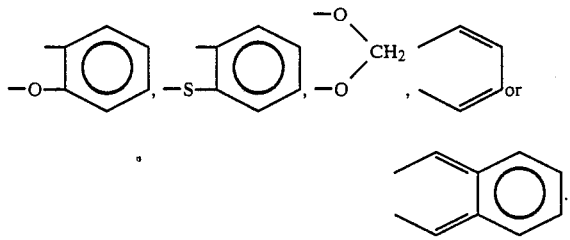

Specific examples of these aromatic compounds include compounds having two benzene rings such as diphenyl, diphenyl ether, diphenyl thioether, diphenylamine and azobenzene, polynuclear aromatic compounds such as naphthalene and anthracene, heterocyclic aromatic compounds such as dibenzofurane, dibenzothiophene and 1,2-methylenedioxybenzene, monosubstituted benzene derivatives such as toluene, aniline, anisole and acetanilide, xylene isomers, methoxytoluene isomers, chlorotoluene isomers and dimethoxybenzene isomers.

According to the process of this invention, the aromatic compound having an electron-donating substituent on the benzene ring is iodinated with iodine in the presence of a solvent.

The amount of iodine used can be properly selected. When it is desired to obtain a monoiodo-aromatic compound, it is about ½ mole per mole of the aromatic compound. For the production of a diiodo-aromatic compound, it is used in an amount of about 1 mole per mole of the aromatic compound. The preferred amount of iodine is, for example, about ½ to about 2 moles per mole of the aromatic compound. In the reaction, all iodine may be added to the reaction at the start of the reaction or in the early stage of the reaction. Or it may be added portionwise as the reaction proceeds. It is not necessary that iodine completely dissolves in the reaction system at the start of the reaction or in the early stage of the reaction.

Examples of the solvent used include halogenated hydrocarbons such as chloroform and dichloromethane, dichloroethane, bromoform, acetic acid, mixtures of these, and mixtures of these with water. A mixture of a halogenated hydrocarbon and acetic acid, and a mixture of a halogenated hydrocarbon, acetic acid and water are preferred. The solvent may contain a small amount of a mineral acid such as sulfuric acid and nitric acid. The amount of such a mineral acid is, for example, up to about 5% by volume. The amount of nitric acid may be less, for example up to about 1% by volume.

The iodination conditions can be properly selected. For example, the iodination is carried out at a temperature of about 10° C. to about 150° C., preferably about 30° C. to about 90° C., and a pressure of atmospheric pressure to about 5 atmospheres, preferably atmospheric pressure to 2 atmospheres. Since the reaction smoothly proceeds under atmospheric pressure, it is not particularly necessary to employ elevated pressures. The reaction can be carried out under relatively mild conditions, for example at a temperature of about 30° to about 90° C. under atmospheric pressure.

In the process of this invention, the aromatic compound having an electron-donating substituent on the benzene ring is iodinated with iodine in the presence of a solvent and at least about ½ mole, preferably about ½ to about 10 moles, per mole of iodine added to the reaction system, of nitrogen dioxide ($NO_2$) added in the form of $NO_2$ to the reaction system. The amount of $NO_2$ added is more preferably about 1 to about 10 moles per mole of iodine added to the reaction system. Amounts of about 1 to about 5 moles, especially about 1 to about 3 moles may be used and frequently preferred.

The mode of adding nitrogen dioxide in the form of $NO_2$ to the iodination reaction system can be properly selected. For example, it may be added as a solution in the solvent used, or may be entrained in an inert gas such as nitrogen gas. Nitrogen dioxide may be introduced into the vapor phase of the reaction zone, or into the liquid phase of the reaction zone; the latter embodiment is preferred. All $NO_2$ may be added at the start of the reaction or in the early stage of the reaction. Or nitrogen dioxide may be introduced portionwise into the reaction either continuously or intermittently during the reaction.

The phrase "adding nitrogen dioxide in the form of $NO_2$ to the iodination reaction system", as used in the present invention, excludes an embodiment in which nitric acid or fuming nitric acid which can generate at least ½ mole, per mole of iodine added, of $NO_2$ to the reaction system is introduced.

The following Examples illustrate the process of this invention in greater detail.

EXAMPLE 1

A 500 ml three-necked glass flask was charged with 17.02 g (100 millimoles) of diphenyl ether, 25.38 g (100 millimoles) of iodine, 0.4 ml of 60% by weight nitric acid and 300 ml of dichloromethane. The flask was immersed in a hot water bath kept at 40° C. While the contents were fully stirred, nitrogen gas containing a predetermined amount of nitrogen dioxide was blown into the solution at a rate of 80 ml/min. During a total reaction period of 16 hours, the amount of nitrogen dioxide added was 10.95 g (238 millimoles).

Analysis of the product by gas chromatography showed that the conversion of diphenyl ether was 100%, and 40.2 g (yield 95.2%) of 4,4'-diiododiphenyl ether, 1.1 g (yield 2.7%) of 2,4'-diiododiphenyl ether and 0.6 g (yield 2.1%) of 4-iododiphenyl ether were formed. The iodination yield (the yield of the iodoaromatic compound based on the used iodine) was 99.0%.

EXAMPLE 2

A 300 ml three-necked glass flask was charged with 13.52 g (100 millimoles) of acetanilide, 12.72 g (50 millimoles) of iodine, 100 ml of acetic acid, 100 ml of chloroform, 10 ml of sulfuric acid and 8 ml of water, and while feeding nitrogen gas containing nitrogen dioxide at a rate of 30 ml/min., the reaction was carried out at 90° C. for 4.5 hours. The total amount of $NO_2$ fed was 4.82 g (105 millimoles).

After the reaction, the product dissolved in chloroform was extracted and separated and quantitatively analyzed by gas chromatography. The conversion of acetanilide was 100%. The yield of 4-iodoacetanilide was 88.0% and the yield of 2-iodo-4-nitroaniline was 2.5%.

Furthermore, 2,4-diiodoacetanilide and diiodobenzene were formed in a yield of 1.5% and 2.5%, respectively. The iodination yield was 98.5%.

EXAMPLE 3

The same reactor as in Example 2 was charged with 10.4 ml (100 millimoles) of 1,2-methylenedioxybenzene, 12.72 g (50 millimoles) of iodine, 150 ml of acetic acid, 50 ml of chloroform, 5 ml of sulfuric acid and 50 ml of water. While nitrogen gas containing $NO_2$ was fed at a rate of 30 ml/min., the reaction was carried out at 90° C. for 9 hours. The total amount of $NO_2$ fed was 5.59 g (121 millimoles).

The reaction product was extracted with chloroform, and analyzed by gas chromatography. The conversion of the starting material was 98.6%. The yield of the resulting 4-iodo-compound was 91.9%, and the yield of the diiodo-compound was 4.0%. The iodination yield was 99.9%.

EXAMPLE 4

The same materials as in Example 3 were charged except that 13.0 ml (100 millimoles) of veratrole was used instead of 1,2-methylenedioxybenzene. The reaction was carried out at 60° C. for 5 hours while blowing nitrogen gas containing $NO_2$ into the solution. The total amount of $NO_2$ fed was 63 millimoles.

The product was analyzed. The conversion of veratrole was 97.9%. The yield of the 4-iodo-compound was 92.5%, the yield of the 4-nitro compound was 1.4%, and the yield of the diiodo-compound was 3.1%. The iodination yield was 98.7%.

EXAMPLE 5

A 500 ml three-necked glass flask was charged with 10.6 g (100 millimoles) of o-xylene, 12.72 g (50 millimoles) of iodine, 200 ml of acetic acid, 100 ml of chloroform, 2 ml of sulfuric acid and 8 ml of water, and the reaction was carried out at 90° C. for 6.5 hours. During this time, 5.31 g (115 millimoles) of $NO_2$ was blown into the reaction system while it was entrained in nitrogen gas.

Gas chromatographic analysis showed that the conversion of o-xylene was 96.2%, the yield of 4-iodoxylene was 77.0% and the yield of 3-iodoxylene was 19.2%.

The iodination yield was 96.2%.

EXAMPLE 6

A 100 ml three-necked glass container was charged with 4.20 g (25 millimoles) of dibenzofurane, 6.35 g (25 millimoles) of iodine, 50 ml of acetic acid, 25 ml of chloroform, 2 ml of sulfuric acid and 2 ml of water, and the reaction was carried out at 90° C. for 6 hours. Nitrogen as containing $NO_2$ was blown into the reaction mixture at a rate of 30 ml/min. The total amount of $NO_2$ fed was 56.5 millimoles.

The reaction product was extracted with chloroform, and analyzed by gas chromatography. There was no unreacted material, and 2,8-diiododibenzofurane and 2-iododibenzofurane were obtained in a yield of 94.6% and 5.4%, respectively. The iodination yield was 97.3%.

EXAMPLE 7

A 500 ml three-necked glass container was charged with 18.33 g (150 millimoles) of p-methylanisole, 19.08 g (75 millimoles) of iodine, 200 ml of acetic acid, 70 ml of chloroform, 7 ml of sulfuric acid and 70 ml of water. While nitrogen gas containing $NO_2$ was being blown into the solution at a rate of 30 ml/min., the reaction was carried out at 60° C. for 5 hours. The total amount of $NO_2$ fed was 4.79 g (104 millimoles).

The reaction product was analyzed by gas chromatography. The conversion of the starting material was 99.0%, and 2-iodo-4-methylanisole was obtained in a yield of 98.5%. The iodination yield was 99.5%.

EXAMPLE 8

A 200 three-necked glass flask was charged with 8.51 g (50 millimoles) of diphenyl ether, 12.6 g (50 millimoles) of iodine, 5.52 g (120 millimoles) of nitrogen dioxide, 0.2 ml (2.6 millimoles) of 60% by weight nitric acid and 150 ml of dichloromethane. The flask was immersed in a hot water bath kept at 39° C., and the reaction was carried out for 8 hours with stirring.

The product was analyzed by gas chromatography. The conversion of diphenyl ether was 100%. There were obtained 19.6 g (yield 93.1%) of 4,4'-diiododiphenyl ether, 0.7 g (yield 3.5%) of 2,4'-diiododiphenyl ether and 0.4 g (yield 2.4%) of 4-iododiphenyl ether. The iodination yield was 97.8%.

EXAMPLE 9

A 200 ml three-necked glass flask was charged with 8.51 g (50 millimoles) of diphenyl ether, 12.69 g (50 millimoles) of iodine, 4 ml of concentrated sulfuric acid, 100 ml of acetic acid and 50 ml of dichloromethane. The flask was immersed in a hot water bath heated at 58° C. While the contents were fully stirred, nitrogen gas containing a predetermined amount of nitrogen dioxide was blown into the solution at a rate of 20 ml/min. During a total reaction period of 3 hours, the amount of nitrogen dioxide fed was 2.85 g (62 millimoles).

The product was analyzed by gas chromatography. The conversion of diphenyl ether was 100%. There were obtained 18.5 g (yield 88%) and 1.90 g (yield 9.0%) of 2,4'-diiododiphenyl ether. The iodination yield was 97%.

EXAMPLE 10

A 200 ml three-necked glass flask was charged with 8.51 g (50 millimoles) of diphenyl ether, 12.9 g (50 millimoles) of iodine, 1.0 ml of concentrated sulfuric acid, 100 ml of acetic acid, 50 ml of dichloromethane and 4 ml of water. The flask was immersed, in a hot water bath kept at 58° C., and while the contents were fully stirred, nitrogen gas containing a predetermined amount of nitrogen dioxide was blown into the solution at a rate of 20 ml/min. During a total reaction period of 3.3 hours, the amount of nitrogen dioxide fed was 4.30 g (93 millimoles).

The product was analyzed by gas chromatography. The conversion of diphenyl ether was 100%. There were obtained 18.8 g (yield 89%) of 4,4'-diiododiphenyl ether, 1.7 g (yield 7.9%) of 2,4'-diiododiphenyl ether and 0.4 g (yield 2.8%) of 4-iododiphenyl ether. The iodination yield was 98.3%.

COMPARATIVE EXAMPLE 1

In the procedure of Example 10, the use of nitrogen dioxide was omitted, and 12 ml of 60% by weight nitric acid was used instead of 1.0 ml of concentrated sulfuric acid.

Specifically, a 200 ml three-necked glass flask was charged with 8.551 g (50 millimoles) of diphenyl ether, 12.6 g (50 millimoles) of iodine, 12 ml (158 millimoles) of 60% by weight nitric acid, 100 ml of acetic acid, 50 ml of dichloromethane and 4 ml of water. The flask was immersed in a hot water bath kept at 58° C., and while the contents were fully stirred, the reaction was carried out for 4 hours.

The product was analyzed by gas chromatography. The conversion of diphenyl ether was 100%. There were obtained 16.7 g (yield 79.3%) of 4,4'-diiododiphenyl ether, 1.2 g (yield 5.7%) of 2,4'-diiododiphenyl ether, 2.2 g (yield 14.6%) of 4-iododiphenyl ether and 0.1 g (yield 0.4%) of 2-iododiphenyl ether.

The reaction was continued, but iodination did not proceed. The iodination yield was 92.5% which was lower than the yield of 98.3% obtained in Example 10.

COMPARATIVE EXAMPLE 2

A 200 ml three-necked glass flask was charged with 8.51 g (50 millimoles) of diphenyl ether, 12.69 g (50 millimoles) of iodine, 2 ml of concentrated sulfuric acid, 50 ml of acetic acid, 15 ml of dichloromethane and 15 ml of water. The flask was immersed in a hot water bath kept at 60° C. While the contents were fully stirred, the reaction was carried out for 2 hours.

The product was analyzed by gas chromatography. The conversion of diphenyl ether was 0.4%, and 4-iododiphenyl ether was formed in an amount of 0.06 g (yield 0.4%).

EXAMPLE 11

A 200 ml three-necked glass flask was charged with 8.51 g (50 millimoles) of diphenyl ether, 12.69 g (50 millimoles) of iodine, 100 ml of acetic acid, 50 ml of dichloromethane and 4 ml of water. The flask was immersed in a hot water bath kept at 60° C. While the contents were fully stirred, nitrogen gas containing a predetermined amount of nitrogen dioxide was blown into the solution at a rate of 30 ml/min. During a total reaction period of 8 hours, the amount of nitrogen dioxide fed was 10.77 g (234 millimoles).

The product was analyzed by gas chromatography. The conversion of diphenyl ether was 100%. There were 19.0 g (yield 90.2%) of 4,4'-diiododiphenyl ether, 1.1 g (yield 5.4%) of 2,4'-diiododiphenyl ether and 6.5 g (yield 4.4%) of 4-iododiphenyl ether. The iodination yield was 97.8%.

EXAMPLE 12

A 200 ml three-necked glass flask was charged with 4.6 g (25 millimoles) of dibenzothiophene, 6.35 g (25 millimoles) of iodine, 50 ml of acetic acid, 25 ml of chloroform, 2 ml of water and 0.2 ml of concentrated sulfuric acid. The flask was immersed in a hot water bath kept at 90° C. While the contents were being fully stirred, nitrogen gas containing a predetermined amount of nitrogen dioxide was blown into the solution at a rate of 30 ml/min. During a total reaction period of 10 hours, the amount of nitrogen dioxide fed was 3.59 g (78 millimoles).

The product was analyzed by gas chromatography. The conversion of dibenzothiophene was 100%. There were obtained 10.6 g (yield 97.1%) of 2,8-diiododibenzofurane and 0.2 g (yield 2.9%) of 2-iododibenzofurane. The iodination yield was 98.6%.

EXAMPLE 13

A 300 ml three-necked glass flask was charged with 9.20 g (100 millimoles) of toluene, 12.72 g (50 millimoles) of iodine, 100 ml of acetic acid, 40 ml of chloroform, 10 ml of water, and 5 ml of concentrated sulfuric acid. The flask was immersed in a hot water bath kept at 60° C., and while the contents were fully stirred, 50 ml of an acetic acid solution containing 13.08 g (284.4 millimoles) of nitrogen dioxide was added dropwise every two hours (9.5 ml each time), and the reaction was carried out for 9 hours.

The product was analyzed by gas chromatography. The conversion of toluene was 98.9%. There were obtained 8.6 g (yield 39.5%) of 2-iodotoluene and 13.2 g (yield 60.5%) of 4-iodotoluene. The iodination yield was 100%.

TABLE 1

| | Starting material mmol | $I_2$ mmol | $NO_2$ mmol | $H_2SO_4$ ml | 60 wt % $HNO_3$ ml (d = 1.38) | Solvent ml | Conditions | Conv. % | Products Yield (%) | Iodination yield (%) |
|---|---|---|---|---|---|---|---|---|---|---|
| Ex. 1 | diphenyl ether 100 | 100 | 238 | — | 0.4 | $CH_2Cl_2$ (300) | 40° C., 16 hrs | 100 | 4,4'-diiododiphenyl ether 95.2<br>2,4'-diiododiphenyl ether 2.7<br>4-iododiphenyl ether 2.1 | 99.0 |
| Ex. 2 | acetanilide 100 | 50 | 105 | 10 | — | $CHCl_3$ + AcOH + $H_2O$ (100 + 100 + 8) | 90° C., 4.5 hrs | " | 4-iodoacetanilide 88.0<br>2-iodo-4-nitroanilide 2.5<br>2,4-diiodoacetanilide 1.5<br>1,4-diiodobenzene 2.5 | 98.5 |
| Ex. 3 | 1,2-methylenedioxybenzene 100 | 50 | 121 | 5 | — | $CHCl_3$ + AcOH + $H_2O$ (50 + 150 + 50) | 90° C., 9 hrs | 98.6 | 4-iodo-1,2-methylenedioxybenzene 91.9<br>diiodo-1,2-methylenedioxybenzene 4.0 | 99.9 |
| Ex. 4 | 1,2-dimethoxybenzene 100 | 50 | 63 | 5 | — | $CHCl_3$ + AcOH + $H_2O$ (50 + 150 + 50) | 60° C., 5 hrs | 97.9 | 4-iodo-1,2-dimethoxybenzene 92.5<br>4-nitro-1,2-dimethoxybenzene 1.4<br>diiodo-1,2-dimethoxybenzene 3.1 | 98.7 |
| Ex. 5 | o-xylene 100 | 50 | 115 | 2 | — | $CHCl_3$ + AcOH + $H_2O$ (100 + | 90° C., 6.5 hrs | 96.2 | 4-iodoxylene 77.0<br>3-iodoxylene | 96.2 |

TABLE 1-continued

| | Starting material mmol | $I_2$ mmol | $NO_2$ mmol | $H_2SO_4$ ml | 60 wt % $HNO_3$ ml (d = 1.38) | Solvent ml | Conditions | Conv. % | Products Yield (%) | Iodination yield (%) |
|---|---|---|---|---|---|---|---|---|---|---|
| Ex. 6 | dibenzo-furane 25 | 25 | 56.5 | 2 | — | CHCl$_3$ + AcOH + H$_2$O (25 + 50 + 2) 200 + 8) | 90° C., 6 hrs | 100 | 19.2 2,8-diiododibenzo-furane 94.6 2-iododibenzofurane 5.4 | 97.3 |
| Ex. 7 | p-methyl-anisole 150 | 75 | 104 | 7 | — | CHCl$_3$ + AcOH + H$_2$O (70 + 200 + 70) | 60° C., 5 hrs | 99 | 2-iodo-4-methylanisole 98.5 | 99.5 |
| Ex. 8 | diphenyl ether 50 | 50 | 120 | — | 0.2 | CH$_2$Cl$_2$ (150) | 39° C., 8 hrs | 100 | 4,4'-diiododiphenyl ether 93.1 2,4'-diiododiphenyl ether 3.5 4-iododiphenyl ether 2.4 | 97.8 |
| Ex. 9 | diphenyl ether 50 | " | 62 | 4 | — | CH$_2$Cl$_2$ + AcOH (50 + 100) | 58° C., 3 hrs | 100 | 4,4'-diiododiphenyl ether 88.0 2,4'-diiododiphenyl ether 9.0 | 97.0 |
| Ex. 10 | diphenyl ether 50 | " | 93 | 1 | — | CH$_2$Cl$_2$ + AcOH + H$_2$O (50 + 100 + 4) | 58° C., 3.3 hrs | 100 | 4,4'-diiododiphenyl ether 89.0 2,4'-diiododiphenyl ether 7.9 4-iododiphenyl ether 2.8 | 98.3 |
| Comp. Ex. 1 | diphenyl ether 50 | " | — | — | 12.0 (158 mmol) | CH$_2$Cl$_2$ + AcOH + H$_2$O (50 + 100 + 4) | 58° C., 4 hrs | " | 4,4'-diiododiphenyl ether 79.3 2,4'-diiododiphenyl ether 5.7 4-iododiphenyl ether 14.6 2-iododiphenyl ether 0.4 | 92.5 |
| Comp. Ex. 2 | diphenyl ether 50 | " | — | 2 | — | CH$_2$Cl$_2$ + AcOH + H$_2$O (15 + 50 + 15) | 60° C., 2 hrs | 0.4 | 4-iododiphenyl ether 0.4 | 100 |
| Ex. 11 | diphenyl ether 50 | " | 234 | — | — | CH$_2$Cl$_2$ + AcOH + H$_2$O (50 + 100 + 4) | 60° C., 10 hrs | 100 | 4,4'-diiododiphenyl ether 90.2 2,4'-diiododiphenyl ether 5.4 4-iododiphenyl ether 4.4 | 97.8 |
| Ex. 12 | dibenzo-thiophene 25 | 25 | 78 | 0.2 | — | CHCl$_3$ + AcOH + H$_2$O (25 + 50 + 2) | 90° C., 10 hrs | 100 | 2,8-diiododibenzothio-phene 97.1 2-iododibenzothiophene 2.9 | 98.6 |
| Ex. 13 | toluene 100 | 50 | 284 | 5 | — | CHCl$_3$ + AcOH + H$_2$O (40 + 100 + 10) | 60° C., 9 hrs | 98.9 | 2-iodotoluene 39.5 4-iodotolyene 60.5 | 100 |

What is claimed is:

1. In a process for producing an iodo-aromatic compound which comprises iodinating an aromatic compound having an electron-donating substituent bonded to the benzene ring with iodine in the presence of a solvent, the improvement wherein the reaction is carried out in the presence of nitrogen dioxide which is added to the reaction system in the form of $NO_2$ in an amount of about ½ to about 10 moles $NO_2$, per mole of iodine added to the reaction system.

2. The process of claim 1 wherein the solvent is selected from the group consisting of halogenated hydrocarbons, acetic acid, mixtures thereof, and mixtures of these with water.

3. The process of claim 1 wherein nitrogen dioxide is added by introducing it continuously or intermittently into the reaction system during the reaction.

4. The process of claim 1 wherein the reaction is carried out at a temperature of about 10° C. to about 150° C.

5. The process of claim 1 wherein the reaction is carried out under atmospheric pressure to about 5 atmospheres.

6. The process of claim 1 wherein the amount of nitrogen dioxide added is about 1 to about 10 moles per mole of iodine added to the reaction system.

7. The process of claim 1 wherein the amount of iodine is about ½ to about 2 moles per mole of the aromatic compound.

8. The process of claim 1 wherein the reaction is carried out in the presence of a small amount of a mineral acid.

9. The process of claim 1 wherein the aromatic compound having an electron-donating substituent bonded to the benzene ring is a compound of the formula

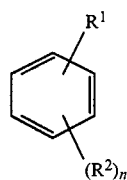

wherein n represents 0, 1 or 2, R¹ represents a member selected from the group consisting of lower alkyl groups, lower alkoxy groups, an amino group, lower acylamino groups, a phenyl group, phenyl group substituted by halogen, phenoxy group, phenoxy group substituted by halogen, phenylthio group, phenylthio group substituted by halogen, phenylamino group and phenylazo group, R² represents a member selected from the group consisting of lower alkyl groups, lower alkoxy groups, Cl and I, and when n is 1, R¹ and R² together may form a group bonded to the adjacent carbon atoms of the benzene ring, and selected from the group consisting of

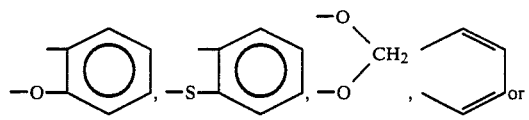

10. The process of claim 9 wherein the aromatic compound is a member selected from the group consisting of diphenyl, diphenyl ether, diphenyl thioether, diphenyl amine, azobenzene, naphthalene, anthracene, dibenzofurane, dibenzothiophene, 1,2-methylenedioxybenzene, toluene, aniline, anisole, acetanilide, xylene isomers, methoxytoluene isomers, chlorotoluene isomers and dimethoxybenzene isomers.

* * * * *